United States Patent [19]

Stormby

[11] 4,203,797
[45] May 20, 1980

[54] METHOD OF AND APPARATUS FOR APPLYING COVER-SLIPS TO SLIDES CARRYING SPECIMENS FOR MICROSCOPIC EXAMINATION

[75] Inventor: Nils G. Stormby, Malmö, Sweden

[73] Assignee: Cytologiska Centrallaboratoriet AB, Sweden

[21] Appl. No.: 947,028

[22] Filed: Sep. 29, 1978

Related U.S. Application Data

[62] Division of Ser. No. 795,007, May 9, 1977, Pat. No. 4,146,414.

[51] Int. Cl.² ............... A01N 1/00; G02B 21/34; A01N 1/00
[52] U.S. Cl. ............................................. 156/521
[58] Field of Search ............... 156/521, 57; 427/2, 427/4; 424/3

[56] References Cited
U.S. PATENT DOCUMENTS 3,819,448  6/1925  Beever ................................ 156/522

Primary Examiner—Sam Silverberg

[57] ABSTRACT

A method of mechanically applying cover-slips onto slides provided with specimens for microscopic examination, wherein the slides are fed to a coating station at which a solvent film is applied without mechanical contact between the coating member and the specimens and then fed to an application station wherein the cover-slips, which have an adhesive layer on the slides thereof arranged to bear against the solvent layer, are applied onto the solvent layer.

4 Claims, 5 Drawing Figures

METHOD OF AND APPARATUS FOR APPLYING COVER-SLIPS TO SLIDES CARRYING SPECIMENS FOR MICROSCOPIC EXAMINATION

This application is a division of copending U.S. patent application Ser. No. 795,007 filed May 9, 1977, now U.S. Pat. No. 4,146,414 the subject matter of which is by reference incorporated herein.

The present invention relates to a method of and apparatus for applying cover-slips to slides carrying specimens for microscopic examination.

Slides are used for instance in pathology and cytology for the microscopy of sections and smears from different types of members and tissues, the specimens being deposited on said slides in very thin sections or in the form of smears. The slides are subsequently coloured in different manners, and then provided with a cover-slip or cover-glass, which is, by means of a transparent mounting, attached on the top of the specimen. Covers of a liquid plastics have been used, which after drying solidify into a transparent layer. If a cover-glass or a plastics coating is used, it must be transparent and possess the optical properties necessary for microscopy with transmitted light, and it also serves as a protective layer for the specimen.

Cover layers or cover-slips, are at present always applied manually. While attempts have been made to make this work more or less mechanical, this has so far been impossible to achieve in an efficient and practical way. Among the difficulties are that the specimens deposited on the slides must not, during the application of the cover-plate, come into contact with extraneous mechanical parts and that the mounting of the cover-slip has to be carried out so as to avoid totally any air inclusions beneath the same.

According to the present invention there is provided a method of mechanically applying cover-slips onto slides provided with specimens for microscopic examination, wherein the slides are fed to a coating station at which a solvent film is applied without mechanical contact between the coating member and the specimens and then fed to an application station wherein the cover-slips, which have an adhesive layer on the sides thereof arranged to bear against the solvent layer, are applied onto the solvent layer.

It has been found that cover slips can be applied in this way without the formation of air inclusions.

Previously adhesive coated foils may be used as cover-slips. It is, of course, preferred and expected that the adhesive will not be tacky until contacted by the solvent which has the primary purpose of activating the adhesive.

The solvent film may be applied to the slides by means of a spreading member, which does not come into contact with the specimens, a solvent "bridge" or layer being maintained between the spreading member and the slide and specimen.

A transparent plastics material in the form of an endless ribbon may conveniently be used for the coverslips, the side of the ribbon arranged to contact the solvent layer being previously provided with the adhesive coating, the adhesive capacity of which is only initiated when the coating comes into contact with said solvent layer. Cover-slips can then be successively severed from the endless ribbon at the time of their application.

During cover-slip application, each cover-slip may be depressed so as to have one end at an angle to the slide this forming a solvent excess in the apex between slide and slip. The cover-slip can then be flattened gradually towards the opposite end of the cover-slip while maintaining the solvent excess in the apex.

The invention also provides a device for the mechanical application of cover-slips onto slides provided with specimens for microscopic examination, including a conveyor for feeding slides into a coating station comprising spreading means for applying without mechanical contact, a solvent film to the slides, and then to an application station comprising means for the application of cover-slips onto said solvent film.

The invention will be more clearly understood from the following description which is given by way of example with reference to the accompanying drawings, in which.

Figure 1:
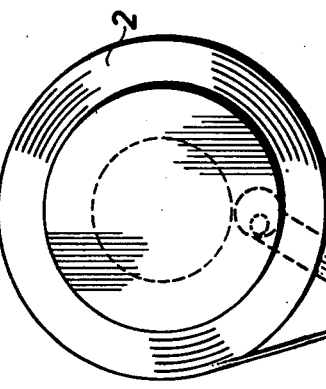
FIG. 1 is a side view of apparatus according to the invention.

In FIG. 1 an endless ribbon of a plastics foil is wound up on a supply spool 2 and has an adhesive coating on the side designed to be brought to bear against the slide. This coating is provided in advance on the plastics foil, and dried to remove solvent prior to being wound, so as to make it possible to wind up the ribbon onto a spool with risk of adjacent turns adhering to one another.

The ribbon 2 is passed over a number of guide rollers to a first driving roller 4, and from there via a severing station 9 to a second driving roller 5. The rollers 4, 5 are driven by belt drive from a master shaft 6.

Slides 7 on which specimens have been placed are simultaneously fed synchronously by a chain conveyor 8 in an essentially horizontal path in a direction towards the driving rollers 5, from a station 7a, and they then pass a coating station for solvent comprising a solvent container 10, which is connected by a feeder tube 16 to a spreading member 11.

The apparatus also includes a roller 12 for the application of the cover-slips, a starting device 13 and a braking mechanism 14, 15.

Figure 5:
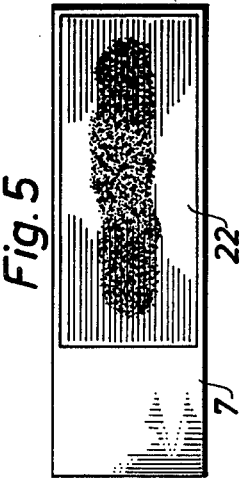
FIG. 5 shows a view of a slide provided with a cover-slip.

A cover-slip applied to the slide 7 is indicated at 22 in FIG. 5. The cover-slip 22 and the slide 7 are, in application, fed at the same velocity, but since the cover-slip 22 is shorter than the slide and as a certain space exists between two subsequent slides 7 on the conveyor 8, the length of the cover-slip fed in a given time is reduced by means of discontinuities in the driving rollers 4 and 5.

Solvent is hermetically enclosed in the container 10, which has a connection to the exterior only through the feeder tube 16. Tube 16 is at its lower end provided with a V-shaped nozzle 11 with a slit opening or a series of apertures across its bottom. The spreading nozzle 11 shaped in this manner is of an appropriate width with respect to the slide. The distance h from the mouth of the feeder tube 16 to the tip of the spreading nozzle 11 is adjusted so as to make the surface tension of the solvent resist the pressure of the column of liquid h when the dispensing nozzle hangs freely in the air. This implies of course, that the solvent cannot drop from the nozzle.

Figure 2:
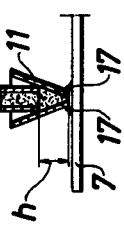
FIGS. 2 and 3 show partial enlargements of the spreading member.
Figure 3:

The device shown in the drawing operates in the following manner: When a slide 7 has been deposited on the belt conveyor 8 at the position 7a the machine will start, whereby the slide 7 is fed along by the conveyor 8 into a position 7b by reason of a cam 14 being rotated one revolution, after which it will temporarily interrupt the feeding movement of the conveyor 8. When a new slide 7 is supplied to the conveyor at the position 7a, the previous slide will be fed from the position 7b to a position 7c and during this process will be coated with solvent layer in the following manner. At the position 7b as shown in an enlarged scale in FIG. 2, the spreading or dispensing nozzle 11 is lowered against the leading end of the now stationary slide, said end being free of the specimen. When the dispensing nozzle contacts the slide a small liquid excess swelling 17 will form, but will be restricted owing to the surface tension. When the slide 7 is then fed along, as indicated by FIG. 3, the dispensing nozzle 11 is somewhat raised from the slide and will thus not come into contact with the specimen. During this movement a liquid film 18 is formed on the slide and spread out from the nozzle over the slide. When the column of liquid h sinks, air can be supplied through the mouth in the feeder tube 16, whereupon new liquid flows down into the nozzle. Immediately before the opposite end of the slide passes the nozzle 11, the nozzle is raised, whereby the liquid film 18 is interrupted.

At the same time as the slides 7 are transferred along on the conveyor the ribbon 2 is fed into a position 19 between rollers 4 and 5, and where a cover strip of a convenient length is severed by means of the device 9.

Figure 4:
FIG. 4 shows a partial enlargement of the method and apparatus of application of the cover-slip.

As the slide 7 reaches the position 7c, a cover-slip of appropriate length is simultaneously fed along into the position 19. At the next feeding operation, the cover-slip will, by means of the feeding rollers 5, be fed down to the roller 12 (see in this connection FIG. 4). In the angle between the cover-slip and the slide a swelling or excess 20 of solvent will form. Thereafter the slide moves relative to the roller 12 so that the cover-slip is pressed down over the length of the slide. The excess 20 of solvent will be pushed along and by this the air is prevented from getting admission, so that the film 21 forming between the cover-slip and the slide will be quite free from air bubbles. The roller 12 is accordingly positioned at a certain distance from the slide, so that a liquid film will at all times remain between the cover-slip and the preparation.

The slide this provided with a cover-slip will then leave the machine by a chute 23 and may then be placed in a drying rack with step-by-step feeding. The entire system can of course be made fully automatic for the depositing as well as the removal of the slides.

I claim:

1. An apparatus for forming a composite assembly of a discrete slide provided with a specimen for microscopic examination and a cover-slip comprising means for transporting a slide having the specimen thereon in a horizontal plane past at least a first and second station, means for positioning a nozzle which dispenses liquid solvent adjacent the surface of the leading end of said slide, means for depositing said solvent directly on said slide and for forming a small but restricted liquid excess swelling thereon, means for partially raising said nozzle from said slide, means for moving said slide through said first station and forming a liquid solvent film on said slide, means for interrupting the formation of the film immediately before the opposite end of the slide passes the nozzle, means for transporting said slide with solvent to said second station, means for feeding a flexible cover-slip toward said slide at said second station, said cover-slip having a pre-applied dry adhesive layer on one side adapted to be activated by said solvent, means for positioning said cover-slip with its leading end first at an angle to said slide while said slide is transported past said second station, means for transporting said slide past said second station at a speed substantially equal to the feeding of said cover slip, means for positioning a roller distinct from said slide and said cover-slip at a predetermined distance above said slide thereby to form an excess of solvent in the angle between the cover slip and the slide and means for simultaneously pressing said cover-slip to said slide from the leading end to the trailing end thereof so as to squeeze any excess solvent and air from between said cover-slip and said slide, and thus from said composite assembly.

2. Apparatus as claimed in claim 1, wherein said means for depositing said solvent includes a solvent container, a feeder tube connected to said solvent container and a spreading member connected to said feeder tube.

3. Apparatus as claimed in claim 1 wherein said means for feeding the cover slips includes a supply spool for receiving an endless flexible cover-strip material ribbon, a plurality of guide and drive rollers for feeding the ribbon and a severing means.

4. Apparatus according to claim 3, wherein said means for feeding includes indexing means for arresting movement of said ribbon at said severing means.

* * * * *